US010369235B2

(12) United States Patent
Chung et al.

(10) Patent No.: US 10,369,235 B2
(45) Date of Patent: Aug. 6, 2019

(54) NON-DIFFUSIVE BOTULINUM TOXIN CAUSING LOCAL MUSCLE PARALYSIS, AND PURIFICATION METHOD THEREOF

(71) Applicant: MEDEXGEN INCORPORATED, Seoul (KR)

(72) Inventors: Yong Hoon Chung, Seoul (KR); Hyun Sub Lee, Seoul (KR)

(73) Assignee: MEDEXGEN INCORPORATED, Seoul (KR)

( * ) Notice: Subject to any disclaimer, the term of this patent is extended or adjusted under 35 U.S.C. 154(b) by 0 days.

(21) Appl. No.: 15/422,129

(22) Filed: Feb. 1, 2017

(65) Prior Publication Data
US 2017/0143849 A1 May 25, 2017

Related U.S. Application Data

(62) Division of application No. 13/700,867, filed as application No. PCT/KR2011/003547 on May 13, 2011, now Pat. No. 9,598,683.

(30) Foreign Application Priority Data

May 31, 2010 (KR) ........................ 10-2010-0051076

(51) Int. Cl.
*A61K 38/48* (2006.01)
*A61K 49/00* (2006.01)
*C12N 9/52* (2006.01)
*G01N 30/96* (2006.01)

(52) U.S. Cl.
CPC ...... *A61K 49/0004* (2013.01); *A61K 38/4893* (2013.01); *A61K 49/00* (2013.01); *C12N 9/52* (2013.01); *C12Y 304/24069* (2013.01); *G01N 30/96* (2013.01)

(58) Field of Classification Search
None
See application file for complete search history.

(56) References Cited

U.S. PATENT DOCUMENTS

| | | | |
|---|---|---|---|
| 3,184,394 A | 5/1965 | Schmidtberger et al. | |
| 3,409,605 A | 11/1968 | Florini | |
| 5,846,929 A | 12/1998 | Johnson et al. | |
| 5,939,070 A | 8/1999 | Johnson et al. | |
| 6,673,598 B1 | 1/2004 | Akers et al. | |
| 6,818,409 B2 | 11/2004 | Oguma | |
| 6,994,859 B1 | 2/2006 | Singh et al. | |
| 7,189,541 B2 | 3/2007 | Donovan | |
| 7,193,066 B1 | 3/2007 | Chaddock et al. | |
| 7,354,740 B2 | 4/2008 | Xiang et al. | |
| 7,452,697 B2 | 11/2008 | Luo et al. | |
| 7,964,199 B1 | 6/2011 | Bigalke et al. | |
| 8,129,139 B2 | 3/2012 | Ton et al. | |
| 8,398,998 B2 | 3/2013 | Bigalke et al. | |
| 8,546,108 B2 | 10/2013 | Ghanshani et al. | |
| 8,927,229 B2 | 1/2015 | Ton et al. | |
| 8,949,033 B2 | 2/2015 | Harakawa et al. | |
| 8,993,268 B2 | 3/2015 | Jung et al. | |
| 9,580,461 B2* | 2/2017 | Linke | B01D 15/166 |
| 9,598,683 B2* | 3/2017 | Chung | A61K 38/4893 |
| 9,719,076 B2* | 8/2017 | Ton | C07K 14/33 |
| 2003/0008367 A1 | 1/2003 | Oguma | |
| 2003/0147921 A1 | 8/2003 | Goodnough et al. | |
| 2004/0028703 A1 | 2/2004 | Bigalke | |
| 2005/0238668 A1 | 10/2005 | Wang et al. | |
| 2006/0211619 A1 | 9/2006 | Steward et al. | |
| 2006/0228777 A1 | 10/2006 | Donovan | |
| 2006/0228780 A1 | 10/2006 | Luo et al. | |
| 2006/0240514 A1 | 10/2006 | Donovan | |
| 2006/0258847 A1 | 11/2006 | Johnson et al. | |
| 2008/0003241 A1 | 1/2008 | Marx et al. | |
| 2009/0123497 A1 | 5/2009 | Luo et al. | |
| 2011/0008843 A1 | 1/2011 | Ton et al. | |
| 2011/0091937 A1 | 4/2011 | Jung et al. | |
| 2011/0171226 A1 | 7/2011 | Johnson et al. | |
| 2011/0217287 A1 | 9/2011 | Bigalke et al. | |
| 2012/0196349 A1 | 8/2012 | Ruegg | |
| 2012/0245324 A1 | 9/2012 | Ton et al. | |

(Continued)

FOREIGN PATENT DOCUMENTS

CN 10-1204577 A 6/2008
KR 10-2003-0060150 A 7/2003

(Continued)

OTHER PUBLICATIONS

De Almeida et al, Pilot study comparing the diffusion of two formulations of botulinum toxin type A in patients with forehead hyperhidrosis/. Dermatology Surgery. Jan. 2007, 33(1 Spec No):S37-43. Abstract Only (Year: 2007).*
Samizadeh et al, Clinical, Cosmetic and Investigational Dermatology. 2018. 11:273-287 (Year: 2018).*
Wohlfarth et al, Neurophysiological Double-Blind Trial of a Botulinum Neurotoxin Type A Free of Complexing Proteins. Clinical Neuropharmacology. Mar.-Apr. 2007. 30/2:86-94. Abstract Only. (Year: 2007).*
Carl J. Malizio et al., "Purification of Clostridium botulinum Type A Neurotoxin", Methods in Molecular Biology: Bacterial Toxins: Methods and protocols, 2000, vol. 145, pp. 27-39, See, abstract and p. 29.

(Continued)

*Primary Examiner* — Nita M. Minnifield
(74) *Attorney, Agent, or Firm* — Novick, Kim & Lee, PLLC; Sang Ho Lee

(57) ABSTRACT

The present invention relates to a method for purifying a non-spreading botulinum toxin that causes local muscle paralysis and a non-spreading botulinum toxin obtained thereby. The method comprises the steps of: subjecting a purified botulinum toxin type A product to ion-exchange chromatography using a controlled pH of buffer, concentration of sodium chloride (NaCl), thereby separating the botulinum toxin type A product into subfractions; and collecting a subfraction having an A260/A280 value in a specific range from the separated subfractions.

3 Claims, 8 Drawing Sheets

(56) References Cited

U.S. PATENT DOCUMENTS

| | | | |
|---|---|---|---|
| 2013/0085267 A1 | 4/2013 | Ton et al. | |
| 2015/0322419 A1 | 11/2015 | Ruegg | |
| 2017/0143849 A1* | 5/2017 | Chung | A61K 38/4893 |
| 2017/0145399 A1* | 5/2017 | Chung | A61K 38/4893 |

FOREIGN PATENT DOCUMENTS

| | | |
|---|---|---|
| KR | 10-2005-0074806 A | 7/2005 |
| KR | 10-2009-0091501 A | 8/2009 |
| WO | 2009142352 A1 | 11/2009 |

OTHER PUBLICATIONS

Frank Gessler et al., "Production and purification of Clostridium botulinum Type C and D Neurotoxin", FEMS Immuninology and Medical Microbiology, 1999, vol. 24, pp. 361-367, See abstract and p. 363.

Chun K. Tse et al., European Journal of Biochemistry, vol. 122, pp. 493-500, 1982, Preparation and Characterization of Homogeneous Neurotoxin type A from Clostridium botulinum.

Sugil Shunji et al., Infection and Immunity, Dec. 1975, vol. 12(6), pp. 1262-1270, Molecular Construction or Clostridium botulinum Type A toxins.

Hideyuki Arimitsu et al., Infection and Immunity, vol. 71(3), Mar. 2003 pp. 1599-1603, Purification of Fully Activated Clostridium Serotype B toxin for treatment of Patients with Dystonia.

Kaoru Inoue et al. Infection and Immunity, vol. 64(5), May 1996, pp. 1589-1594, Molecular Compositions of Clostridium botulinum Type a Progenitor toxins.

J. Melling et al., "Clostridium Botulinum Toxins: Nature and Preparation for Clinical Use", Eye (1998) 2, pp. 16-23.

J.A. Kauffman, et al., "Comparison of the Action of Types A and F Botulinum Toxin at the Rat Neuromuscular Junction" Pathology Division, U.S. Army Medical Research Institute of Infectious Diseases, Fort Detrick, MD, Aug. 22, 1984.

H. Sugiyama et al, "Improved Procedure for Crystallization of Clostridium botulinum Type A Toxic Complexes," Applied and Environmental Micorbiology, pp. 963-966, Apr. 1977.

M. Kersher, et al., "Comparison of the Spread of three botulinum toxin type A preparations," Division of Biochemistry and Molecular Biology, Cosmetic Science, University of Hamburg, Oct. 15, 2011.

* cited by examiner (A)

(B)

(A)

(B)

(A)

(B)

NON-DIFFUSIVE BOTULINUM TOXIN CAUSING LOCAL MUSCLE PARALYSIS, AND PURIFICATION METHOD THEREOF

TECHNICAL FIELD

The present invention relates to a method for purifying a non-spreading botulinum toxin that causes local muscle paralysis and a non-spreading botulinum toxin obtained thereby.

BACKGROUND ART

The US Food and Drug Administration (FDA) warned that Botox® which is used for cosmetic purposes such as wrinkle removal can cause serious side effects, such as death, in severe cases.

The US FDA said that a side effect of muscle paralysis in areas other than an area injected with Botox® was reported and persons injected with Botox® were hospitalized or died.

In addition, the US FDA said that patients in which serious Botox® side effects occurred were mostly child patients whose leg muscles were injected with Botox® in order to treat muscular stiffness caused by cerebral palsy.

Botox® is widely used for the treatment of the muscles of cerebral palsy patients, neck muscle stiffness, pain caused by muscular stiffness, and vocal cord palsy. In the field of cosmetic therapy, Botox® is used for the removal of wrinkles and the prevention or treatment of aging. As anti-aging therapies have recently been popularized, the amount of Botox® used has increased annually.

When Botox® is injected into muscles, the muscular nerves are paralyzed. Thus, Botox® has been injected into children with cerebral palsy whose leg muscles are excessively stiff, in order to make walking more natural.

The FDA considers that Botox® influences respiratory muscle function while spreading to areas other than legs, thereby causing side effects [FDA NEWS RELEASE FOR IMMEDIATE RELEASE Apr. 30, 2009, FDA Patient Safety News: Show #74, April 2008]. In connection with this, the FDA said that patients and doctors need to pay attention to whether a decrease in breathing rate or difficulty in swallowing occurs after injection with Botox® [FDA-approved Patient Labeling Jul. 31, 2009 APPENDIX 1: MEDICATION GUIDE BOTOX, BOTOX Cosmetic (Boe-tox®) (on a botulinum toxin A) for Injection)].

However, the FDA said that a serious side effect of Botox® injection for cosmetic purposes such as wrinkle removal has not yet been reported. The FDA did not require doctors to stop Botox® treatments for cosmetic purposes.

The US consumers union asked the FDA to strengthen the warning that 180 cases of Botox®-related side effects were reported to the FDA between the years 1997 and 2006 and 16 cases thereof led to death and that the use of Botox® can cause abnormalities.

In prior art, botulinum toxin has been purified by performing acid precipitation (U.S. Pat. No. 7,354,740, entitled "Animal product free system and process for purifying a botulinum toxin", Allergan, Inc.) or performing chromatography following acid precipitation (U.S. Pat. No. 7,452,697, entitled "Chromatographic method and system for purifying a botulinum toxin", Allergan, Inc; Korean Patent Application No. 10-2008-0016800, entitled "Method of purifying botulinum toxin from *Clostridium botulinum*, Medexgen Inc.; Korean Patent Application No. 10-2002-0000685, entitled "Method for purifying Clostridium botulinum type A toxin", Medexgen Inc.).

However, it is known that the botulinum toxins purified by the above methods significantly spread to areas in the body other than the injected area to paralyze the surrounding organs or respiratory muscles, and in severe cases, cause serious side effects leading to death.

DETAILED DESCRIPTION OF THE INVENTION

Technical Problem

Therefore, the present invention has been made in view of the above-mentioned problems, and the present inventors have found that, when an existing botulinum toxin type A purified by either acid precipitation or chromatography following acid precipitation is subjected to ion-exchange chromatography using sodium chloride, three heterogeneous subfractions are obtained, and one subfraction thereof has muscle-paralyzing activity and, at the same time, does not spread in the body.

Therefore, it is an object of the present invention to provide a non-spreading botulinum toxin, which does not spread in the body and, at the same time, localize muscle-paralyzing activity, and a method for purifying the same.

Technical Solution

To achieve the above objects, in accordance with one aspect of the present invention, there is provided a method for purifying a non-spreading botulinum toxin, comprising the steps of: separating the botulinum toxin type A product into subfractions by conducting ion-exchange chromatography using pH 4.5-6.5 buffer and 0.02-0.2 M of sodium chloride (NaCl);and collecting a non-spreading botulinum toxin subfraction, which has an A260/A280 value of 0.4-0.6.

In accordance with still another aspect of the present invention, there is provided a non-spreading botulinum toxin preparation, which is purified by the above method comprises, Zn, Fe and Mg ion concentrations at least 150, 80, and 140 ppb per 100 U/ml, respectively.

In accordance with still another aspect of the present invention, there is provided a method for determining a non-spreading botulinum toxin, comprising: injecting the non-spreading botulinum toxin into the either left or right hind limb calf muscle of mouse(4-6 wk old, weighing 18-22 g) in an amount equivalent to 1.5-3 times the $LD_{50}$ of the toxin; and determining whether the right hind limb muscles and respiratory muscles of the mouse were paralyzed and whether the mouse died.

In accordance with still another aspect of the present invention, there is provided the said method, wherein the non-spreading botulinum toxin preparation shows a survival rate at least 80% at 96 hours after injection of 2 U toxin preparation in the volume 50 μL either left or right hind limb calf muscle of mouse(4-6 wk old, weighing 18-22 g).

Advantageous Effects

According to the present invention, a non-spreading botulinum toxin that causes local muscle paralysis can be obtained which causes muscle paralysis in a desired area, does not spread to other areas from administration site and has the effect of paralyzing muscles in a fast and lasting manner.

Also, it is possible to obtain a non-spreading botulinum toxin having a high toxin titer compared to conventional botulinum toxin products.

In addition, according to the present invention, a non-spreading botulinum toxin which is not mixed with a spreading toxin can be obtained in large amounts by controlling anion chromatographic conditions.

BEST MODE FOR CARRYING OUT THE INVENTION

Figure 1:
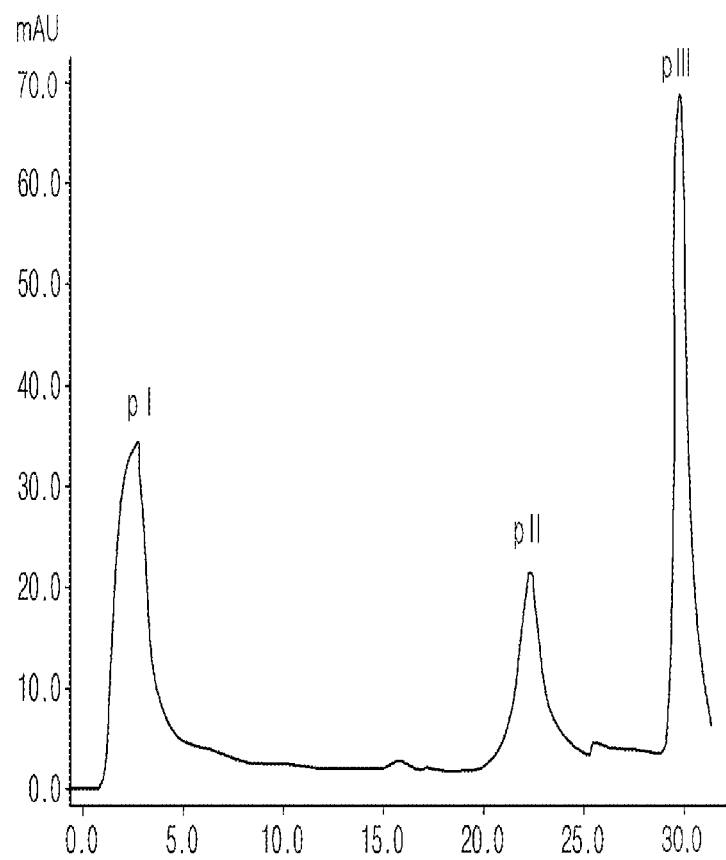
FIG. 1 shows the results of separating botulinum toxin into subfractions by ion-exchange chromatography in Example 1.

Hereinafter, each step of a method for purifying a non-spreading botulinum toxin according to the present invention will be described in further detail.

A method for purifying a non-spreading botulinum toxin according to the present invention comprises the steps of: separating the botulinum toxin type A product into subfractions by conducting ion-exchange chromatography using buffer of pH 4.5-5.5, using 0.02-0.2M of sodium chloride (NaCl); and collecting a non-spreading botulinum toxin subfraction, which has an A260/A280 value of about 0.4-0.6.

The inventive method for purifying a non-spreading botulinum toxin is a method wherein an existing botulinum toxin obtained by either acid precipitation or ion-exchange chromatography following acid precipitation is subjected to a novel ion-exchange chromatographic method developed by the present inventors, thereby obtaining a non-spreading botulinum toxin fraction.

Thus, the inventive method for purifying a non-spreading botulinum toxin is performed using a botulinum toxin type A obtained by either acid precipitation from a culture broth of a *Clostridium botulinum* type A strain or chromatographic purification after acid precipitation.

When the purified botulinum toxin type A is subjected to ion-exchange chromatography using sodium chloride, three subfractions can be obtained from the ion-exchange resin. To perform the ion-exchange chromatography, sodium acetate buffer is used, and the concentration of sodium chloride that is added to the buffer in order to obtain gradually increased subfractions, and each separated fraction is taken. It was found that, when no sodium chloride was used (0 M of NaCl), the fraction separated was an active fraction (peak I, pI) which spreads in the body, and when sodium chloride was used at a concentration of 0.02-0.2 M, the fraction separated was an active fraction (peak II, PII) which does not spread in the body, and when sodium was used at a concentration of 1 M, the fraction separated was an inactive fraction (peak III, pIII) which spreads in the body.

Specifically, the concentration of sodium chloride that is used to obtain fraction pII is in the range of 0.02 to 0.2 M, and when no sodium chloride is used or the concentration of sodium chloride is out of the above range, fraction pII can contain the pI or pIII fraction, suggesting that it is difficult to obtain a non-spreading active fraction having a local muscle-paralyzing effect sought by the present invention.

Meanwhile, when the ion-exchange chromatography is performed using sodium chloride in a buffer having a pH ranging from 4.5 to 5.5, the amount of the pI or pIII fraction in the separated subfractions is reduced, and the purity of the pII fraction increases. This can be confirmed by comparing the A260/A280 values or measuring the degree of paralysis upon injection into the right hind limb muscles of mice.

Moreover, when the ion-exchange chromatography is performed using sodium chloride such that the amount of a purified botulinum toxin type A sample is ⅕-1 time the volume of the ion-exchange chromatography column used, the amount of the pII fraction increases. Specifically, when the column volume is 1 ml and the amount of the purified botulinum toxin type A sample is 0.2-1 ml, the amount of the pII fraction obtained is in the range of 20% to 50%.

Meanwhile, it was found that the pII fraction obtained by the inventive method for purifying the non-spreading botulinum toxin type A has a total $LD_{50}$ of $1\times10^5$-$5\times10^5$ U/ml, as measured using mice. In addition, it can be seen that the pII fraction does not spread to areas other than a desired area upon injection and it initiates muscle paralysis within a significantly short time and maintains muscle paralysis for a long time compared to a commercially available product.

In addition, the pII fraction obtained by the inventive method for purifying the non-spreading botulinum toxin comprises, per 100 U/ml, at least 150 ppb of Zn ions, at least 80 ppb of Fe ions and at least 140 ppb of Mg ions.

The inventive method for purifying the non-spreading botulinum toxin is characterized in that the contents of Mg, Fe and Zn are significantly higher than those of a botulinum toxin type A toxin purified by a conventional method.

It was found that, when the non-spreading botulinum toxin obtained by the purification method of the present invention was injected into the right hind limbs of mice in an amount equivalent to 1.5-3 times the $LD_{50}$ of the toxin, the right hind limb muscles were paralyzed, whereas it did not paralyze respiratory muscles and had no lethal activity, suggesting that the non-spreading botulinum toxin of the present invention does not spread in the body.

MODE FOR CARRYING OUT THE INVENTION

Hereinafter, the present invention will be described in detail with reference to examples and the accompanying drawings, but the scope of the present invention is not limited to these examples and drawings.

A commercially available product used in the examples of the present invention is a Botox product (Allergan, Inc) prepared by the method disclosed in U.S. Pat. No. 7,354,740 [entitled "Animal product free system and process for purifying a botulinum toxin"]. However, the present invention is applied not only to the above commercially available product or botulinum toxin type A products purified by the above method, but also to any botulinum toxin type A product purified by acid precipitation.

EXAMPLE 1

Fractionation by Ion-exchange Chromatography

A sample purified from a botulinum toxin culture medium by acid precipitation was subjected to ion-exchange chromatography, thereby separating the sample into three subfractions. The results of the chromatography are shown in FIG. 1 [pI, peak I (an active fraction that spreads in the body); pII, peak II (an active fraction that does not spreads in the body); pIII, peak III (an inactive fraction)].

The ion-exchange chromatography was performed using an AKTA FPLC instrument (GE Healthcare), a Hitrap DEAE FF column (GE healthcare), and sodium acetate buffer (pH 5.5) as running buffer (elution buffer).

Specifically, the sample was eluted with 0 M NaCl (pH 5.5) in sodium acetate to obtain an unbound wash fraction (pI, an active fraction that spreads in the body), and then eluted 0.05 M NaCl to obtain a fraction (pII, an active fraction that does not spread in the body), and eluted with 1M NaCl to obtain a fraction (pIII, an inert fraction). The sample was subjected to acid precipitation at a flow rate of 1 ml/min, followed by desalting.

EXAMPLE 2

Figure 2:
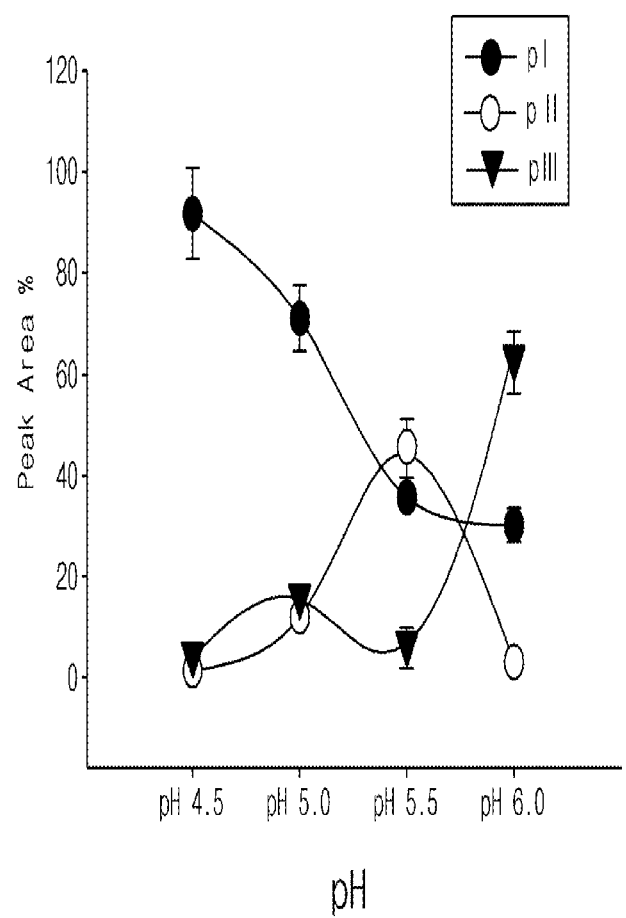
FIG. 2 is a graphic diagram showing changes in the peak areas % of subfractions according to changes in the pH of buffer.

Changes in Peaks and Characteristics as a Function of Changes in the pH of Buffer FIG. 2 shows the peak areas % of the subfractions according to the changes in the pH of the buffer used in the ion-exchange chromatography. As can be seen in FIG. 2, when the pH of the buffer was in the range of 4.5 to 5.5, the peak area % of the pII fraction increased. Table 1 below shows the A260/A280 values of the subfractions as a function of the pH of the buffer, and Table 2 below shows the total $LD_{50}$ (unit) of the subfractions.

TABLE 1

| | A260/A280 | | | |
|---|---|---|---|---|
| | pH 4.5 | pH 5.0 | pH 5.5 | pH 6.0 |
| pI | 0.76 ± 0.15 | 0.69 ± 0.09 | 0.67 ± 0.05 | 0.63 ± 0.08 |
| pII | 0.50 ± 0.05 | 0.55 ± 0.04 | 0.55 ± 0.03 | 0.81 ± 0.19 |
| pIII | 0.76 ± 0.10 | 0.82 ± 0.13 | 0.84 ± 0.12 | 0.79 ± 0.09 |

As can be seen in the above Table 1, when the pH of the buffer was in the range of 4.5 to 5.5, the A260/A280 value of the pII fraction was in the range of 0.45 to 0.6, suggesting that the pII fraction is suitable for administration.

Thus, it is preferable to adjust the pH of the buffer to 4.5-5.5 in order to obtain a purified active fraction (pII) that does not spread in the body.

TABLE 2

| | Total $LD_{50}$ (Unit) | | | |
|---|---|---|---|---|
| | pH 4.5 | pH 5.0 | pH 5.5 | pH 6.0 |
| Conventional product (pre-sample) purified by acid precipitation | 5 ± 0.8 | 5 ± 1 | 5 ± 0.8 | 5 ± 1.2 |
| pI | 1.5 ± 0.4 | 3 ± 0.5 | 2 ± 0.4 | 2 ± 0.8 |
| pII | 0.2 ± 0.2 | 1 ± 0.2 | 3 ± 0.4 | 0.4 ± 0.2 |
| pIII | — | 0.2 ± 0.1 | 0.2 ± 0.1 | 2 ± 1 |

(Unit: $10^5$ U)

As can be seen in the above Table 2, when the pH of the buffer was in the range of 5.0 to 5.5, the total $LD_{50}$ of the pII fraction was in the range of $0.8 \times 10^5$ to $3.5 \times 10^5$ U/ml, suggesting that return rate of pII is relatively high.

Thus, it is preferable to adjust the pH of the buffer to 4.5-5.5 in order to obtain a safe active fraction (pII) that does not spread in the body.

EXAMPLE 3

Figure 3:
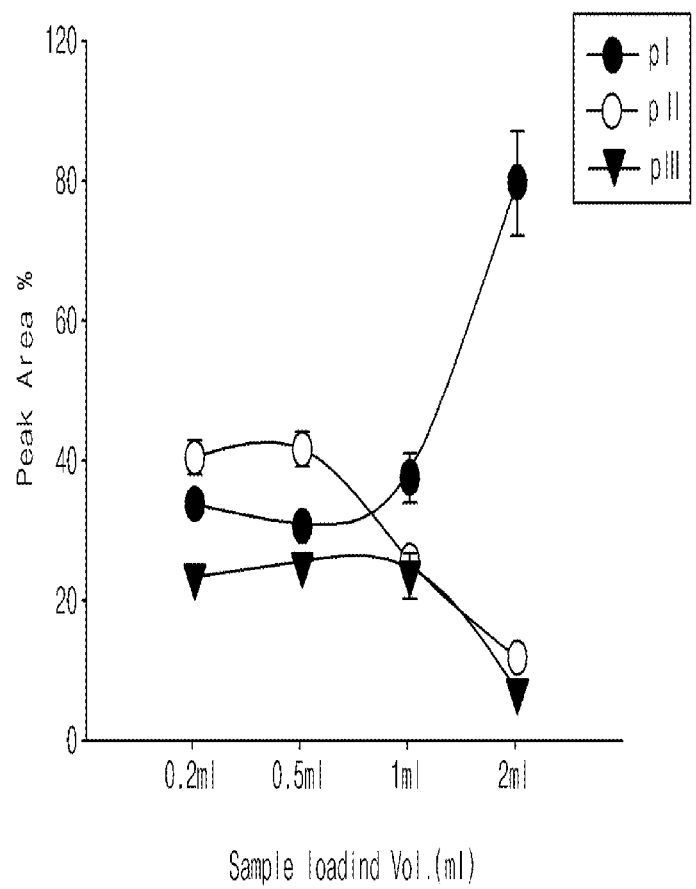
FIG. 3 is a graphic diagram showing a change in the peak area % of each subfraction according to the loading volume of a sample.

Changes in Peaks and Characteristics as a Function of Changes in Sample Loading Volume Subfractions were obtained in the same manner as in Example 1. FIG. 3 shows changes in the peak area % of the subfractions (pI, pII and pIII) as a function of changes in the loading volume of the sample used to obtain the subfractions. Also, Table 3 shows changes in the A260/A280 values of the subfractions as a function of the sample loading volume, and Table 4 below shows changes in the total $LD_{50}$ (unit) of the subfractions as a function of the sample loading volume.

TABLE 3

| | A260/A280 | | | |
|---|---|---|---|---|
| | 0.25 ml | 0.5 ml | 1 ml | 2 ml |
| pI | 0.67 ± 0.08 | 0.64 ± 0.07 | 0.68 ± 0.09 | 0.67 ± 0.13 |
| pII | 0.55 ± 0.02 | 0.56 ± 0.01 | 0.55 ± 0.04 | 0.55 ± 0.03 |
| pIII | 0.85 ± 0.14 | 0.84 ± 0.09 | 0.82 ± 0.18 | 0.84 ± 0.24 |

As can be seen in the above Table 3, when the sample loading volume was in the range of was 0.25 to 2 ml, the A260/A280 of the pII fraction was 0.4-0.6, suggesting that it is adjustable sample for administration.

Thus, it is preferable to control the sample loading volume in the range of ⅕ to 2 times the column volume in order to obtain a large amount of an active fraction (pII) that does not spread in the body.

TABLE 4

| | Total $LD_{50}$ (unit) | | | |
|---|---|---|---|---|
| | 0.25 ml | 0.5 ml | 1 ml | 2 ml |
| Conventional product (pre-sample) purified by acid precipitation | 2.5 ± 0.5 | 5 ± 1 | 10 ± 4 | 20 ± 5 |
| pI | 0.8 ± 0.2 | 1.6 ± 0.4 | 5 ± 2 | 15 ± 4.8 |
| pII | 1.6 ± 0.2 | 4 ± 0.6 | 4 ± 0.9 | 4 ± 1.5 |
| pIII | 0.2 ± 0.1 | 0.4 ± 0.1 | 0.8 ± 0.2 | 0.6 ± 0.3 |

(Unit: $10^5$ U)

As can be seen in the above Table 4, when the sample loading volume was in the range of 0.25 to 1 ml, the total $LD_{50}$ of the pII fraction was in the range of $0.8\times10^5$ to $3.5\times10^5$ U/ml, suggesting that pII return rate is relatively high.

Thus, it is preferable to control the sample loading volume in the range of ⅕ to 2 times the column volume in order to obtain a safe active fraction (pII) that does not spread in the body.

TEST EXAMPLE 1

Comparison of Muscle-paralyzing Effects

1) Injection into Right Hind Limb Muscles

In order to examine the muscle-paralyzing effects of the subfractions obtained in Example 1, injection into the right hind limb muscles of mice was performed.

Figure 4:
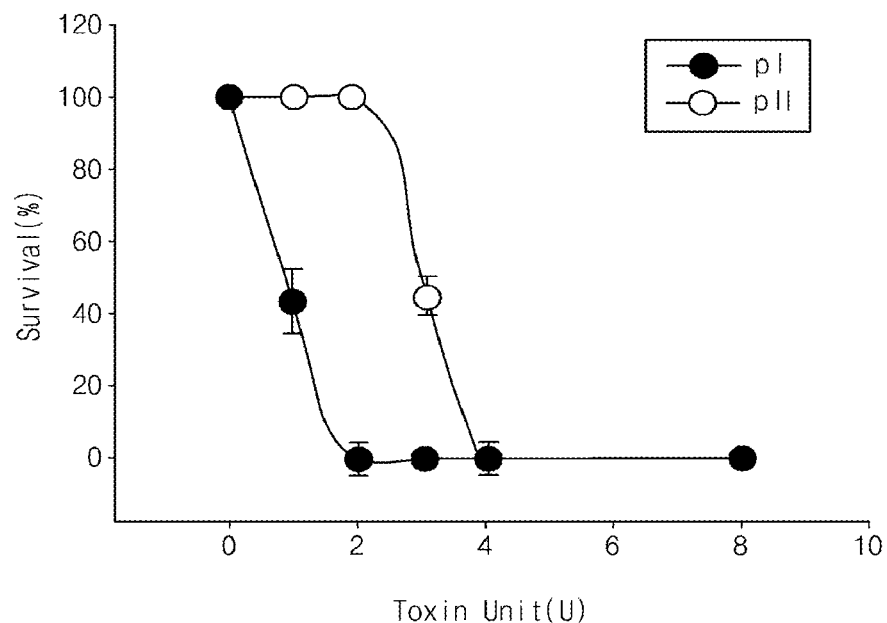
FIG. 4 shows survival rates according to changes in the dose (A) and time after administration (B) of active fractions (pI and pII) among the subfractions separated in Example 1 [Mouse: ICR, female, 4 week-old, 18-22 g, n=10, IM injection into right hind leg].
Figure 4:
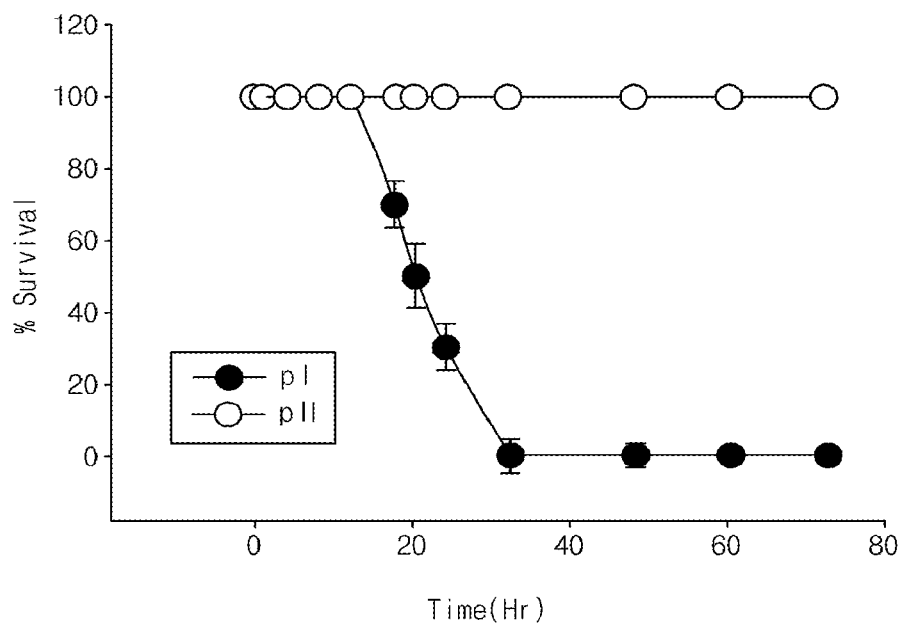

ICR mice (female, 4 week-old, 18-22 g) were divided into three groups, each group consisting of 10 mice. The weight of each mouse was precisely measured and recorded. Each of the subfractions was filled into a 50 μL Hamilton syringe at a concentration of 1 U/20 μL in the absence of air, and then the syringe needle was pricked into the right hind leg ankle of each ICR mouse to a depth of about 3 cm, and each of the subfractions was injected into the muscles of each mouse. After injection into the muscles, limb paralysis score for each mouse was evaluated at various time points according to the criteria shown in Table 5, and the survival rate of the mice was measured. The results of the measurement are shown in FIG. 4.

TABLE 5

| Score | Criteria |
|---|---|
| 0 | Limb appearance and walking of normal mice |
| 1 | Mice walk with dragging, but toes are not put together. |
| 2 | Together with criterion of 1, toes are put together. |
| 3 | Together with the criterion of 2, foot joints are bent inward. |
| 4 | Together with the criterion of 3, feet come into contact with leg muscles, and legs are lame. |

TABLE 6

| Fractions | Area paralyzed upon injection into right hind limbs of mice |
|---|---|
| Active fraction that spreads in the body | Various areas in the body, including right hind limb, diaphragm, etc. |
| Active fraction that does not spread in the body | Right hind limb |
| Inactive fraction that spreads in the body | — |

As can be seen in FIG. 4, among the subfractions obtained in Example 1, the active fraction (pII) that does not spread in the body showed a significant increase in the dose versus survival rate compared to the active fraction (pI) that spreads in the body (FIG. 4A), and the survival rate at a dose of 2 U was 100% for the pII fraction and 0% for the pI fraction, which extremely differ from each other (FIG. 4B).

TEST EXAMPLE 2

Comparison of Diffusion to the Body between Commercial Product and Active Fraction (pII) that does not Spread in the Body In order to examine the muscle-paralyzing effects of a commercial product (Allergan's Botox) and the subfraction pII obtained in Example 1, injection into the right hind limb muscles of mice was performed.

Figure 5:
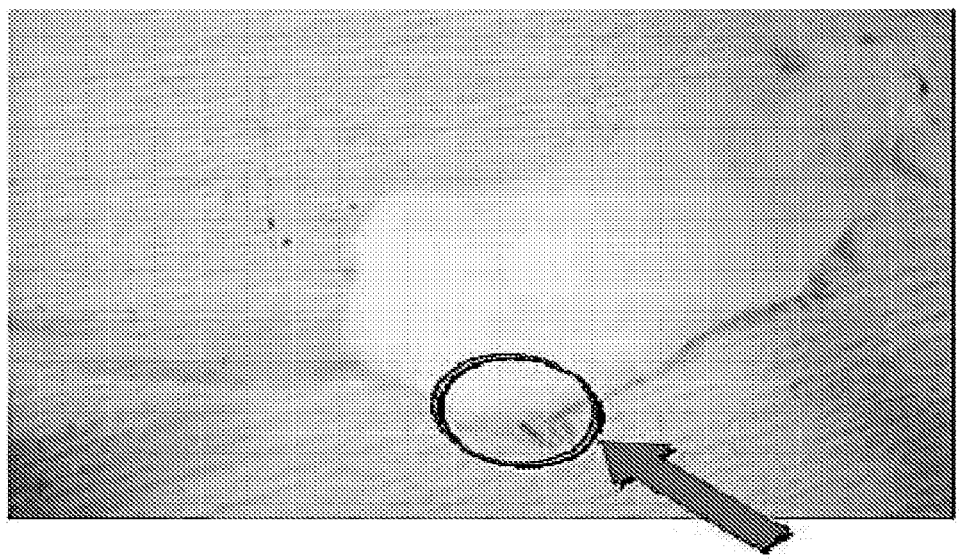
FIG. 5 is a set of photographs showing a comparison of diffusion to the body from administration site measured at 12 hours after a non-spreading active fraction (pII) among the subfractions separated in Example 1 and a commercially available product were administered into the right hind limbs of mice.
Figure 5:
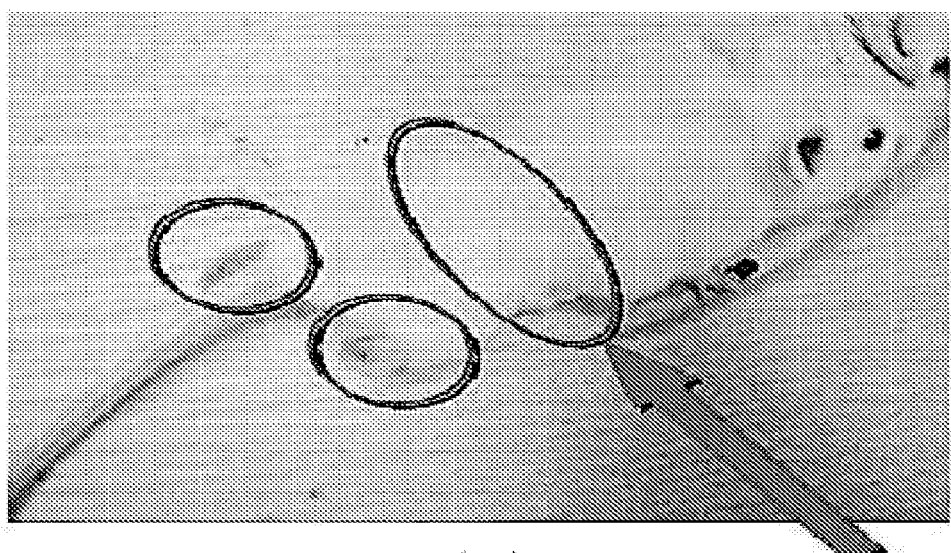
Figure 6:
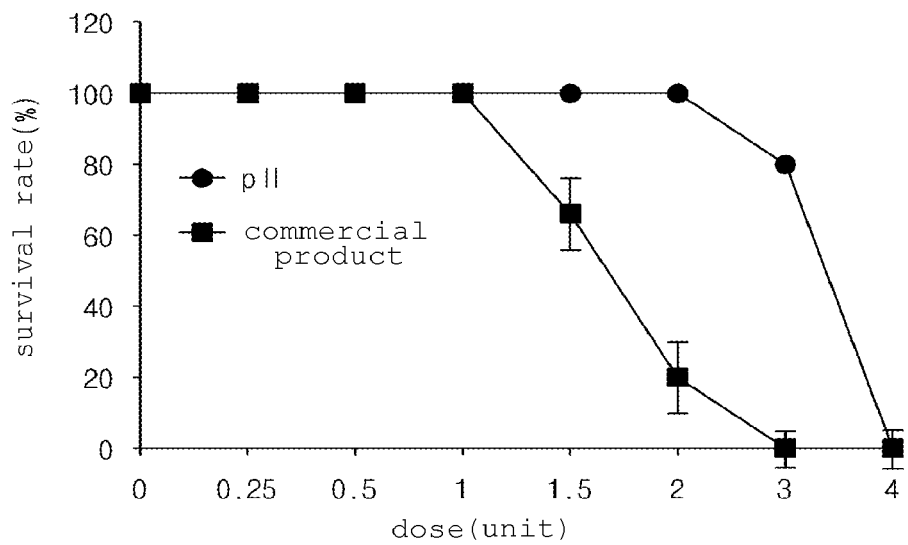
FIG. 6 is a set of graphs showing survival rates according to dose (A) and time after administration (B), measured after a non-spreading active fraction (pII) among the subfractions separated in Example 1 and a commercially available product were administered into the right hind limbs of mice.
Figure 6:
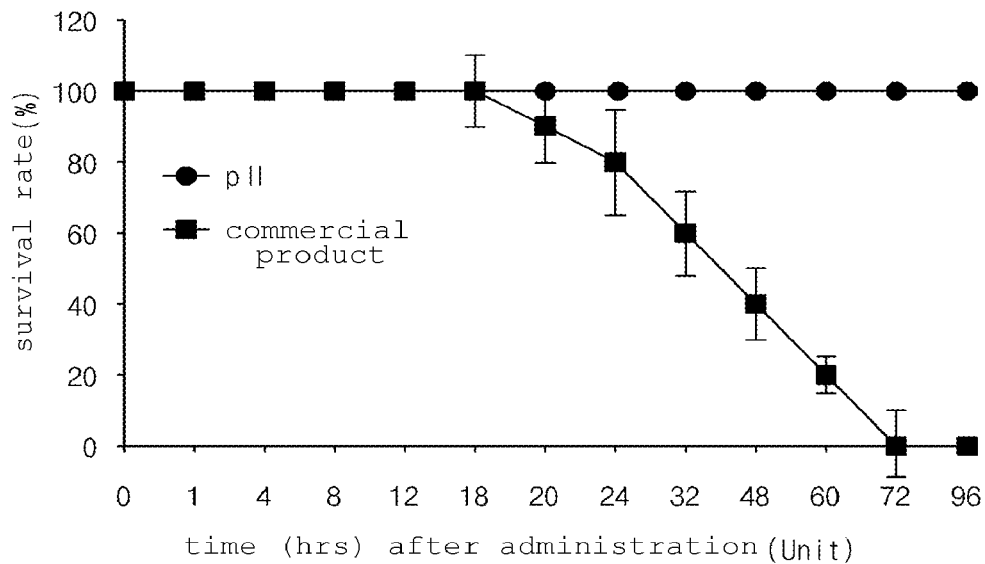

ICR mice (female, 4 week-old, 18-22 g) were divided into two groups, each group consisting of 10 mice. The weight of each mouse was precisely measured and recorded. Each of the commercial product and the subfraction pII was filled into a 50 μl Hamilton syringe at a concentration of 1 U/20 μl in the absence of air, and then the syringe needle was pricked into the right hind leg ankle of each ICR mouse to a depth of about 3 cm, and each of the commercial product and the subfraction was injected into the muscles of each mouse. After injection into the muscles, the degree of paralysis of the mice was visually observed in order to determine the in vivo spread of the commercial product and the subfraction. FIG. 5 shows the state of the mice photographed at 12 hours after injection, and FIG. 6 shows the survival rate of mice as a function of dose and administration time. In addition, FIG. 7 shows the time of initiation of the muscle-paralyzing effect, and FIG. 8 shows the lasting time of the muscle-paralyzing effect.

As can be seen in FIG. 5, the subfraction pII paralyzed only the right hind limb into which it was intramuscularly injected, but the commercial product did spread to and paralyzed the waist and the opposite limb.

As can be seen in FIG. 6, the subfraction pII showed a significant increase in the dose versus survival rate compared to the commercial product (FIG. 6A), and the survival rate at a dose of 2 U was 100% for the pII subfraction and 0% for the commercial product, which extremely differ from each other (FIG. 6B).

Figure 7:
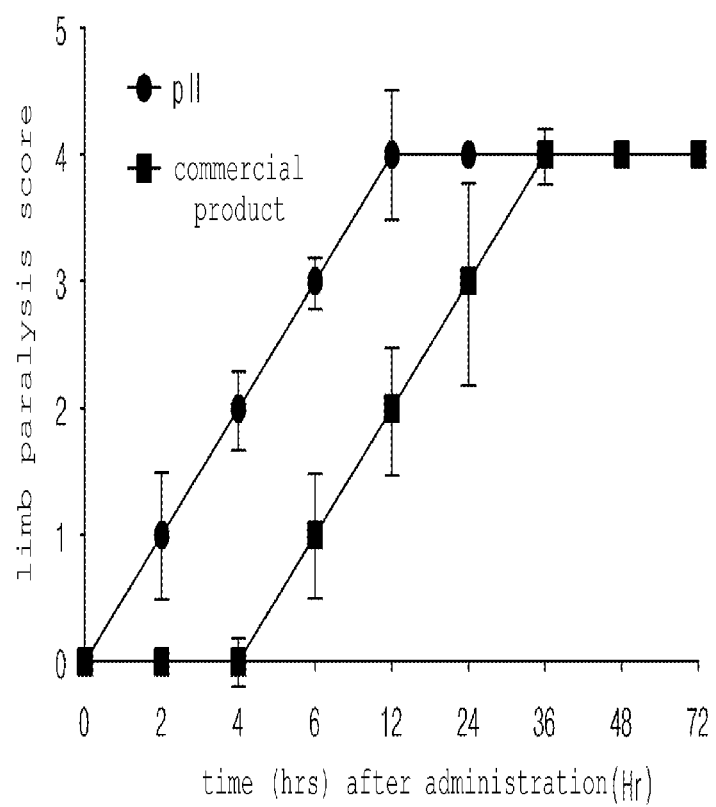
FIG. 7 shows a comparison of the time of initiation of muscle paralysis, measured after 1 U of each of a non-spreading active fraction (pII) among the subfractions separated in Example 1 and a commercially available product were administered into the right hind limbs of mice.
Figure 8:
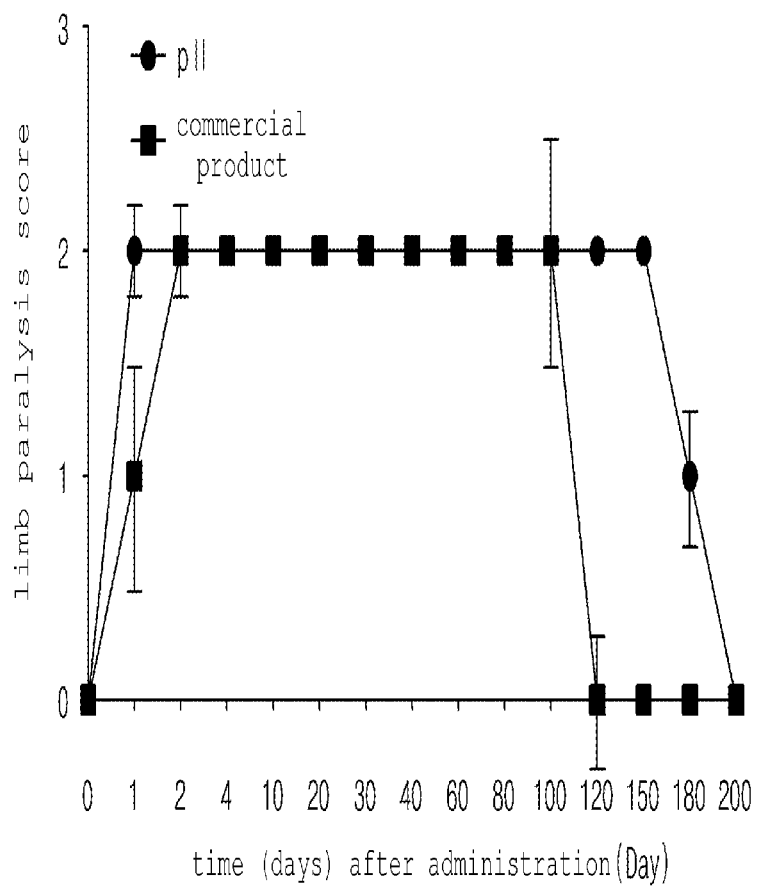
FIG. 8 shows a comparison of the lasting time of muscle paralysis, measured after 0.5 U of each of a non-spreading active fraction (pII) among the subfractions separated in Example 1 and a commercially available product were administered into the right hind limbs of mice.

As can be seen in FIG. 7, the pII subfraction initiated the muscle-paralyzing effect at a dose of 1 U within a significantly short time compared to the commercial product.

As can be seen in FIG. 8, the lasting time of the muscle-paralyzing effect of the pII subfraction was longer than that of the commercial product by 80 days or more at a dose of 0.5 U.

TEST EXAMPLE 3

Analysis of Ion Contents of Freeze-dried Botulinum Toxins

A commercial product (Allergan's Botox) and the subfraction pII obtained in Example 1 were freeze-dried and the ion contents thereof were analyzed.

For comparison with the commercial product, the diluted pII fraction and the same amount of botulinum toxin (100 U) were freeze-dried with additives, and a mouse lethal test was used to confirm the freeze-dried products of the commercial product and the pII subfraction had the same activity, after which the ion contents of the freeze-dried products were analyzed. Specifically, each of the two freeze-dried products was dissolved in 10 ml of distilled water, and then the ion contents thereof were measured using an inductively coupled plasma mass spectrometer. The results of the measurement are shown in Table 7 below.

TABLE 7

|  | Mg | Fe | Zn |
|---|---|---|---|
| pII | 183.0 ± 19.3* | 105.4 ± 22.1** | 332.6 ± 140.8*** |
| Commercial product | 78.1 ± 7.4* | 39.6 ± 3.3 | 65.6 ± 25.9 |

*$p < 0.0015$,
**$p < 0.011$,
***$p < 0.045$

As can be seen in the above Table 7, the contents of Mg, Fe and Zn in the freeze-dried product of the non-spreading botulinum toxin (pII fraction) purified by the present invention were significantly higher than those in the commercial product.

Although the preferred embodiments of the present invention have been described for illustrative purposes, those skilled in the art will appreciate that various modifications, additions and substitutions are possible, without departing from the scope and spirit of the invention as disclosed in the accompanying claims.

INDUSTRIAL APPLICABILITY

According to the present invention, a non-spreading botulinum toxin that causes local muscle paralysis can be obtained in large amounts. This non-spreading botulinum toxin causes muscle paralysis in a desired area, does not spread to areas other than the desired area and has the effect of paralyzing muscles in a fast and lasting manner.

The invention claimed is:

1. A method for determining a non-spreading botulinum toxin, comprising:
    injecting the non-spreading botulinum toxin into the either left or right hind limb calf muscle of mouse (4-6 wk old, weighing 18-22 g) in an amount equivalent to 1.5-3 times the LD50 of the toxin in the volume ranges of 20-50 µL; and
    assessing paralysis conditions of the hind limb muscles and respiratory muscles of the injected mouse and a survival rate of the injected mouse to determine a non-spreading botulinum toxin.

2. The method of claim 1, wherein the non-spreading botulinum toxin shows a survival rate at least 80 % at 96 hours after injection of 2 U toxin preparation in the volume 50 µL either left or right hind limb calf muscle of the mouse.

3. The method of claim 2, wherein the paralysis conditions comprises:
    limb appearance and walking of normal mice;
    mice walk with dragging, but toes are not put together;
    mice walk with dragging, toes are put together;
    mice walk with dragging, toes are put together, foot joints are bent inward; and
    mice walk with dragging, toes are put together, foot joints are bent inward, feet come into contact with leg muscles, and legs are lame.

* * * * *